United States Patent
Medvedev et al.

(10) Patent No.: US 8,613,696 B2
(45) Date of Patent: Dec. 24, 2013

(54) NON-INVASIVE DIAGNOSTICS FOR VENTRICLE ASSIST DEVICE

(75) Inventors: Alexander Medvedev, Ann Arbor, MI (US); Muhammad K. Sami, Ypsilanti, MI (US); Masamichi Yanai, Ann Arbor, MI (US)

(73) Assignee: Thoratec Corporation, Pleasanton, CA (US)

( * ) Notice: Subject to any disclaimer, the term of this patent is extended or adjusted under 35 U.S.C. 154(b) by 116 days.

(21) Appl. No.: 13/209,814

(22) Filed: Aug. 15, 2011

(65) Prior Publication Data

US 2013/0046129 A1  Feb. 21, 2013

(51) Int. Cl.
*A61N 1/362* (2006.01)

(52) U.S. Cl.
USPC .......................................................... 600/16

(58) Field of Classification Search
USPC .................................................... 600/16, 17
See application file for complete search history.

(56) References Cited

U.S. PATENT DOCUMENTS

| | | | |
|---|---|---|---|
| 5,965,089 A | 10/1999 | Jarvik et al. | |
| 6,066,086 A | 5/2000 | Antaki et al. | |
| 6,572,530 B1 * | 6/2003 | Araki et al. | 600/17 |
| 6,716,189 B1 | 4/2004 | Jarvik et al. | |
| 6,949,066 B2 | 9/2005 | Bearnson | |
| 6,991,595 B2 | 1/2006 | Burke et al. | |
| 7,033,147 B2 | 4/2006 | Yanai et al. | |
| 7,160,243 B2 | 1/2007 | Medvedev | |
| 7,175,588 B2 | 2/2007 | Morello | |
| 7,284,956 B2 | 10/2007 | Nose et al. | |
| 7,645,225 B2 | 1/2010 | Medvedev et al. | |
| 7,850,594 B2 | 12/2010 | Sutton et al. | |
| 7,951,062 B2 | 5/2011 | Morello | |
| 7,963,905 B2 | 6/2011 | Salmonsen et al. | |
| 2007/0142923 A1 | 6/2007 | Ayre et al. | |
| 2007/0265703 A1 | 11/2007 | Sutton et al. | |
| 2009/0005632 A1 | 1/2009 | Schima et al. | |
| 2010/0042259 A1 | 2/2010 | Simons | |
| 2010/0174231 A1 | 7/2010 | Horvath et al. | |
| 2011/0015465 A1 | 1/2011 | Ayre et al. | |
| 2011/0054239 A1 | 3/2011 | Sutton et al. | |
| 2011/0160519 A1 | 6/2011 | Arndt et al. | |
| 2011/0313238 A1 | 12/2011 | Reichenbach et al. | |

OTHER PUBLICATIONS

R. Kosaka, et al., Operating Point Control System for a Continuous Flow Artificial Heart: In Vitro Study, ASAIO Journal 2003, pp. 259-264.

Mitsuo Oshikawa, et al., Detection of Total Assist and Sucking Points Based on the Pulsatility of a Continuous Flow Artificial Heart: In Vivo Evaluation, ASAIO Journal 1998, pp. M704-M707.

Kenji Araki, et al., Detection of Total Assist and Sucking Points Based on Pulsatility of a Continuous Flow Artificial Heart: In Vitro Evaluation, ASAIO Journal 1998, pp. M708-M711.

* cited by examiner

*Primary Examiner* — Eric D. Bertram

(57) ABSTRACT

A circulatory assist system has a pump with a motor coupled to rotate the pump at a selectable speed. A controller drives the motor at a target speed and collects blood flow measurements during operation of the pump. An impaired flow condition is identified when a plurality of successive blood flow measurements are between an expected minimum flow and a low flow threshold, such that the low flow would necessitate issuing an alert. During the impaired flow condition, it is detected whether an inflow obstruction exists by determining whether a reduction in speed of the pump is correlated with a predetermined increase in the blood flow measurements. If the inflow obstruction is detected, then the speed of the pump is further reduced to further increase the blood flow measurements.

4 Claims, 8 Drawing Sheets

| RPM | LPM | PI | |
|---|---|---|---|
| ↓ | ↑ | ↓ | = Inflow Obstruction |
| ↓ | ↓ | ↑ | = Outflow Obstruction |

Fig. 7

| RPM | Q | PI | Obstruction |
|---|---|---|---|
| Down | Large Jump | Large Drop | Inflow Probable |
| | | Small Drop | Inflow Possible |
| Down | Small Jump | Large Drop | Inflow Likely |
| | | Small Drop | No Call |
| Down | No Large Change | No Large Change | Saturated Flow |
| Down | Large Drop | Large Jump | Outflow Probable |
| | | Small Jump | Outflow Possible |
| Down | Small Drop | Large Jump | Outflow Likely |
| | | Small Jump | No Call |

Fig. 8

NON-INVASIVE DIAGNOSTICS FOR VENTRICLE ASSIST DEVICE

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to blood circulatory assist devices, and, more specifically, to autonomous control of a pump to maintain optimum blood flow under a variety of conditions including partial obstructions and low blood volume.

Many types of circulatory assist devices are available to either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart, Inc., of Ann Arbor, Mich. One embodiment of the DuraHeart® system may employ a centrifugal pump with a magnetically levitated impeller to pump blood from the left ventricle to the aorta. An electric motor magnetically coupled to the impeller is driven at a speed appropriate to obtain the desired blood flow through the pump.

A typical cardiac assist system includes a pumping unit, electrical motor (e.g., a brushless DC motor integrated into the pump), drive electronics, microprocessor control unit, and an energy source such as rechargeable batteries. The system may be implantable, either fully or partially. The goal of the control unit is to autonomously control the pump performance to satisfy the physiologic needs of the patient while maintaining safe and reliable system operation. A control system for varying pump speed to achieve a target blood flow based on physiologic conditions is shown in U.S. Pat. No. 7,160,243, issued Jan. 9, 2007, which is incorporated herein by reference in its entirety. Thus, a target blood flow rate may be established based on the patient's heart rate so that the physiologic demand is met. The control unit may establish a speed setpoint for the pump motor to achieve the target flow. Whether the control unit controls the speed setpoint in order to achieve flow on demand or whether a pump speed is merely controlled to achieve a static flow or speed as determined separately by a physician, it is essential to automatically monitor pump performance to ensure that life support functions are maintained.

The actual blood flow being delivered to the patient by the assist device can be monitored either directly by sensors or indirectly by inferring flow based on motor current and speed. Despite the attempt by the control unit to maintain a target flow, various conditions such as obstructions of the inflow conduit or outflow conduit from the pump, low blood volume due to dehydrations, or other problems may cause the blood flow to decrease. Low flow and no flow alarms are conventionally employed to indicate conditions when the blood flow through the pump has inadvertently fallen below a low flow threshold or a no flow threshold, respectively. The alarms may comprise warning sounds, lights, or messages to allow the patient or caregiver to take corrective action. In order to provide a greater safety margin, it would be desirable to identify and correct flow problems before the low flow or no flow thresholds are reached.

SUMMARY OF THE INVENTION

In one aspect of the invention, a method is provided for controlling a pump motor in an assist device for pumping blood of a patient. An actual pump flow value of the pump motor is monitored during pumping of the blood by the assist device. An expected minimum pump flow value is determined corresponding to nominal pump operation for the monitored speed and current flow. When the actual pump flow value is greater than the expected minimum pump flow value, a target speed of the pump motor is set according to predetermined criteria (which may comprise a predefined setpoint as determined by a physician, for example). When the actual pump flow value is less than the expected minimum pump flow value for at least a first diagnostic wait time, a pump flow diagnostic state is entered.

In an embodiment, the pump flow diagnostic state comprises entering a low pump flow state if the actual pump flow value is less than a low flow threshold for at least a low flow wait time. The low flow threshold is less than the expected minimum pump flow value, and the low pump flow state includes generating a low flow warning. A no pump flow state is entered if the actual pump flow value is less than a no flow threshold for at least a no flow wait time. The no pump flow state includes generating a no flow warning, wherein the no flow threshold is less than the low flow threshold, and wherein the no flow wait time is less than the low flow wait time. An obstructed flow diagnostic state is entered if the actual pump flow value is less than the expected minimum pump flow value for at least an obstruction diagnostic wait time, wherein the obstruction diagnostic wait time is greater than the low flow wait time.

In an embodiment, the obstructed flow diagnostic state comprises selectably modifying the target speed of the pump motor and monitoring the resultant actual pump flow value. An inflow obstruction is detected if a reduction in target speed is correlated with a predetermined increase in the resultant actual pump flow value. If an inflow obstruction is detected, then the target speed is selectably decreased to a new target that substantially maximizes the actual pump flow value.

In an embodiment, the obstructed flow diagnostic state comprises detecting an outflow obstruction if a reduction in target speed is correlated with a predetermined decrease in the resultant actual pump flow value. If an outflow obstruction is detected, then the target speed is selectably increased to a new target until either a predetermined maximum speed or an actual pump flow value substantially equal to the expected minimum pump flow value is obtained.

In an embodiment, changes in pulsatility associated with the modified speed of the pump motor are also used to detect an inflow or outflow obstruction.

BRIEF DESCRIPTION OF THE DRAWINGS

FIG. 7 is a matrix showing general correlations of pump speed, flow, and pulsatility with inflow and outflow obstructions.

FIG. 8 is a more detailed decision matrix for one preferred embodiment.

DETAILED DESCRIPTION OF PREFERRED EMBODIMENTS

Figure 1:
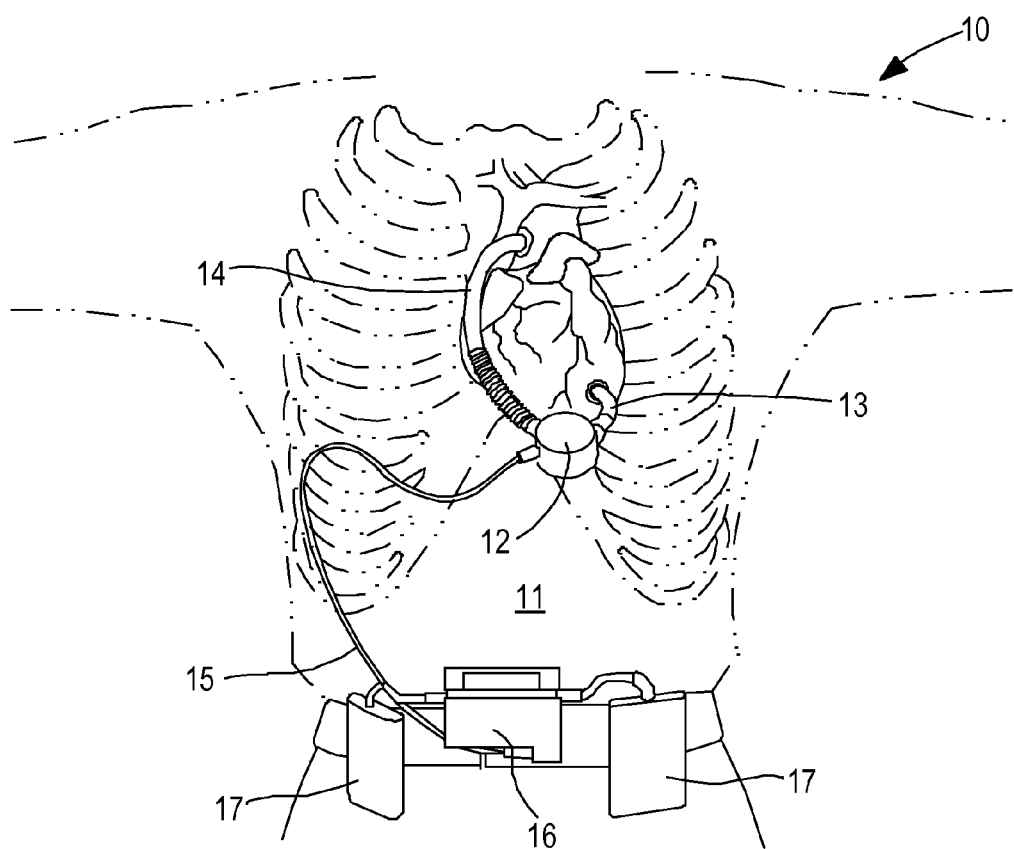
FIG. 1 is a block diagram of a circulatory assist system of a type employing the present invention.

Referring to FIG. 1, a patient 10 is shown in fragmentary front elevational view. Surgically implanted into the patient's abdominal cavity 11 is the pumping portion 12 of a ventricular assist device. An inflow conduit 13 conveys blood from the patient's left ventricle into the pumping portion 12, and an outflow conduit 14 conveys blood from the pumping portion 12 to the patient's ascending thoracic aorta. A power cable 15 extends from the pumping portion 12 outwardly of the patient's body via an incision to a compact controller 16. A power source, such as a battery pack worn on a belt about the patient's waist, and generally referenced with the numeral 17, is connected with controller 16.

Each of the conduits 13 and 14 may include a tubular metallic housing proximate the pumping portion 12 which may connect to elongated segments extending to the heart and ascending aorta, respectively. At the end of inflow conduit 13 connected to the patient's heart (preferably at the apex of the left ventricle), and at the end of outflow conduit 14 connected to the ascending thoracic aorta, the conduits are generally attached to the natural tissue by sutures through the use of a sewing ring or cuff so that blood flow communication is established and maintained. The distal end of the inflow conduit 13 is inserted through the ventricle wall and into the heart in order to establish blood flow from the heart to the pumping portion 12.

Figure 2:
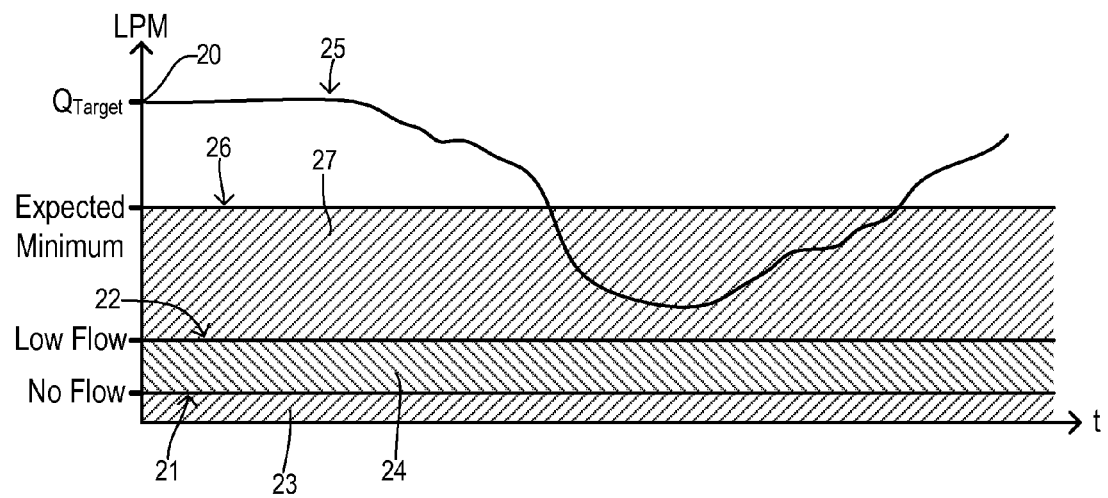
FIG. 2 is a graph showing changes in volumetric flow occurring during operation of a circulatory assist system.

FIG. 2 illustrates a target flow $Q_{Target}$ at 20 and an actual flow value 25 that varies over time. A no flow threshold 21 and a low flow threshold 22 define no flow region 23 and low flow region 24, respectively, wherein appropriate alarms are generated by a pump control unit whenever actual flow dips into these regions. The trajectory of actual pump flow value 25 may fall to a value below an expected minimum flow threshold 26 into a respective diagnostic region 27. Expected minimum flow threshold 26 may be obtained from a lookup table or a model based on empirically derived flow profiles that result from various inflow or outflow obstructions or various reductions in blood volume. The present invention is configured to detect operation in region 27 and to take steps to identify a potential cause and a remedy in order to increase flow if possible.

When the actual flow falls below an expected minimum flow that should be present in view of the operating speed of the pump (i.e., assuming no obstructions and proper blood volume), the present invention enters a diagnostic state for identifying a potential cause of the impaired flow such as a partial or complete obstruction of the inflow conduit or the outflow conduit, or a condition wherein a flow is saturated for a given pump speed due to a limited blood volume resulting from dehydration, etc.

Figure 3:
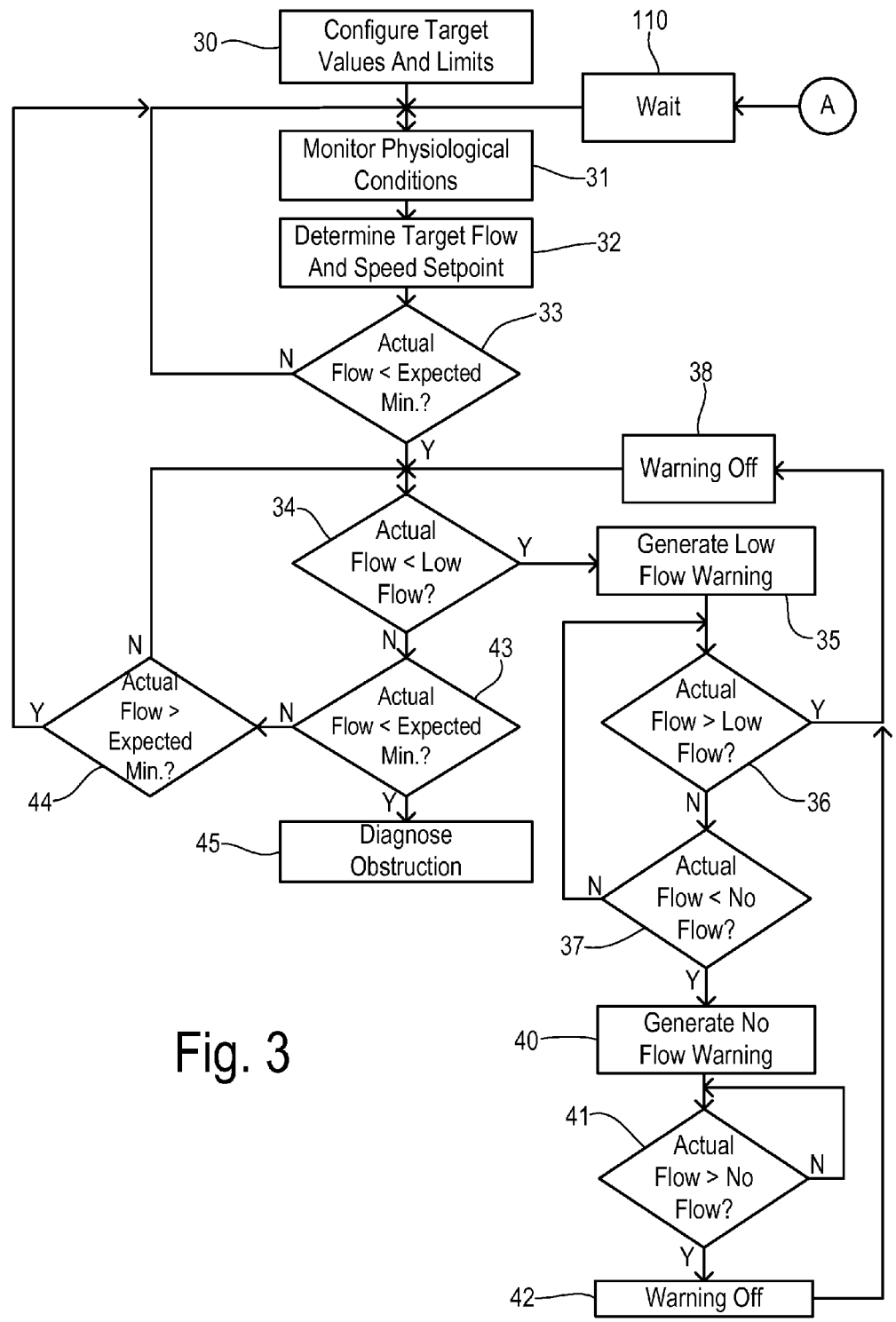
FIG. 3 is a flowchart showing one preferred method of the invention.

As shown in FIG. 3, a method of the invention begins in step 30 wherein a physician or other medical practitioner configures target values and performance limits pertaining to blood flow rate and pump speed to be provided for a particular patient. The circulatory assist device then monitors for physiological conditions such as heart rate or pump pulse rate in step 31. In step 32, a target flow rate and a target speed (i.e., setpoint speed) are determined and used for controlling the system as known in the art. Alternatively, a speed setpoint may be determined according to other predetermined criteria such as a setpoint configured according to a static value chosen by a physician for the particular patient. A check is performed in step 33 to determine whether the actual (i.e., indirectly estimated) pump flow value ($eLPM_{pump}$) is less than an expected minimum pump flow value ($LPM_{ExpMin}$) for greater than a diagnostic wait time ($T_{FlowDiagWait}$). As mentioned above, $eLPM_{pump}$ is an estimated average pump flow for a given pump speed. If not, then a return is made to step 31 and pump operation continues normally with the pump speed being determined by a target flow that is set according to physiological conditions.

If the actual pump flow value is less than the expected minimum flow value in step 33, then a check is made in step 34 to determine whether the actual flow is less than a low flow threshold ($LPM_{LowFlow}$). In particular, step 34 preferably requires that the actual flow value be less than $LPM_{LowFlow}$ for greater than a predetermined low flow wait time ($T_{LowFlowWait}$). When $eLPM_{pump} < LPM_{LowFlow}$ then a low flow warning is generated in step 35. A low flow state is then entered while the low flow warning continues. Checks are made in step 36 to determine whether the actual flow value has risen above the low flow threshold for greater than the low flow wait time, and a check is made in step 37 to determine whether the actual flow value is less than a no flow threshold ($LPM_{NoFlow}$) for at least a no flow wait time ($T_{NoFlowWait}$). The value of $T_{NoFlowWait}$ is less than the value of $T_{LowFlowWait}$ so that detection of a no flow condition has priority. If the actual flow value rises above the low flow threshold, then the warning is turned off in step 38 and a return is made to step 34. If an actual flow value falls below the no flow threshold for the no flow diagnostic wait time, then a no flow warning is generated in step 40 to indicate that a greater urgency of taking corrective action. While in a no flow warning state, a check is made in step 41 to determine whether the actual flow value rises above the no flow threshold for longer than the no flow wait time. When it does, the no flow warning is turned off in step 42, the low flow warning is turned off in step 38, and a return is made to step 34.

When step 34 determines that the actual flow value has not stayed below the low flow threshold for the low flow diagnostic wait time, then a check is made in step 43 to determine whether the actual flow value stays below the expected minimum flow value for at least an obstruction diagnostic wait time ($T_{ObsDiagWait}$) which is longer than both the low flow diagnostic wait time and the no flow diagnostic wait time. If not, then a check is made in step 44 to determine the actual flow value has recovered above the expected minimum flow value for at least the diagnostic wait time ($T_{FlowDiagWait}$), and if so, then a return is made to step 31 for nominal pump control. If the condition is not true in step 44, then a return is made to step 34 for continuing to monitor for either a low flow condition or an obstructed condition. When the condition in step 43 is satisfied then the method proceeds to step 45 wherein a potential obstruction is diagnosed as described below.

Figure 4:
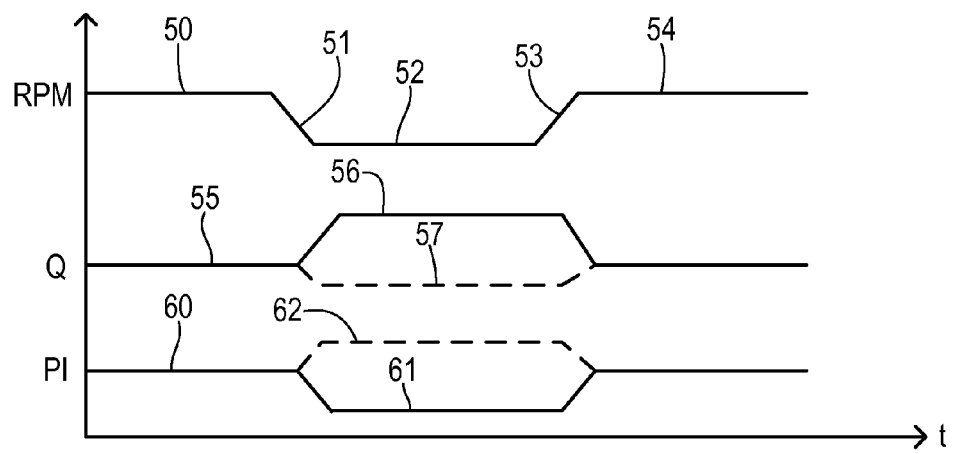
FIG. 4 is a graph illustrating certain changes in flow and pulsatility that may be associated with changes in pump speed under certain conditions.

The present invention is based in part on an observation that a nominal reduction in pump speed generally results in an increase in flow if an inflow obstructions exists. As shown in FIG. 4, a pump is operating at a first speed at 50, but then a speed reduction 51 to a lower speed 52 is deliberately introduced. After a sufficient time to allow flow to stabilize at a new value for measurement, speed then increases at 53 back to the original speed at 54. An actual pump flow Q has an original value at 55 will rise to a higher flow at 56 during a reduced pump speed at 52 in the event that an inflow obstruction exists. If an outflow obstruction exists, then the actual flow instead decreases as shown at 57 during the time of reduced pump speed 52.

The change in pump speed may also affect the pulsatility index (e.g., the difference between the maximum and minimum flows divided by the average maximum flow) such that an initial pulsatility at 60 decreases to a value at 61 in the presence of an inflow obstruction when pump speed is reduced at 52. On the other hand, in the presence of an outflow obstruction the pulsatility will increase at 62 during the speed reduction. Inspection of the change in flow resulting from a deliberate speed reduction may be sufficient to differentiate between an inflow obstruction and an outflow obstruction, but it may be coupled with an inspection of the change in pulsatility to potentially improve an identification.

Figure 5:
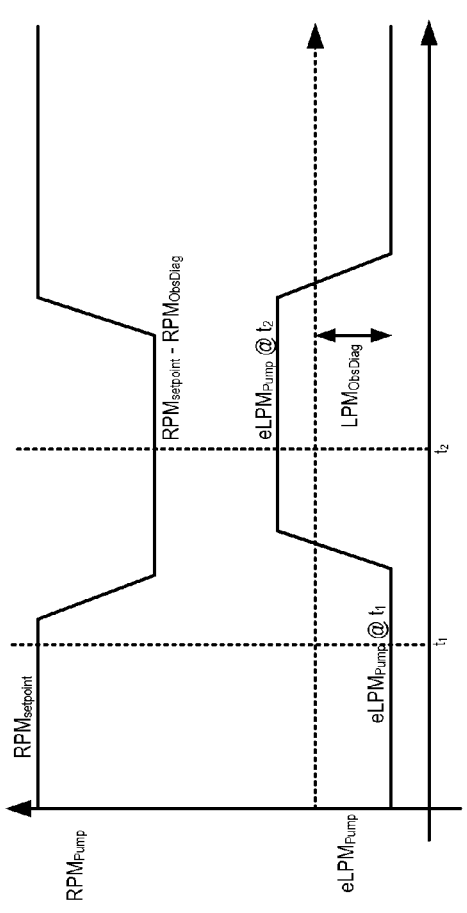
FIGS. 5 and 6 are graphs showing large and small flow increases that may be associated with a reduction in pump speed.
Figure 6:
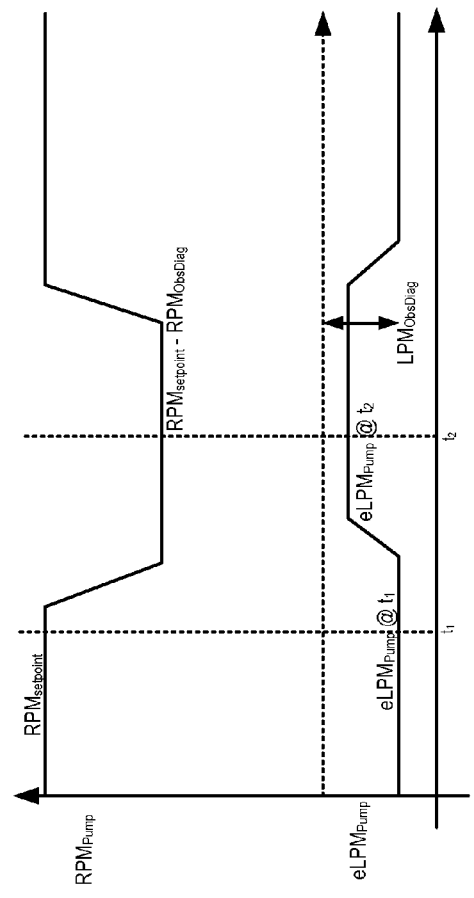

The diagnostic relationships employed by the present invention are shown in greater detail in FIGS. 5 and 6. FIG. 5 shows an inflow obstruction wherein a pump speed $RPM_{setpoint}$ and a pump flow $eLPM_{pump}$ are measured at a first time $t_1$. Pump speed is reduced by a predetermined speed of $RPM_{ObsDiag}$ at a time $t_2$. At time $t_2$, the actual pump flow has stabilized at a new value representing an increase by more than a threshold designated $LPM_{ObsDiag}$, which indicates the presence of the inflow obstruction. In a preferred embodiment, a plurality of speed modification trials of the type shown in FIG. 5 are repeated in order to gather statistics for increasing a confidence level in detecting the inflow obstruction.

In FIG. 6, the actual flow through the pump increases during the speed reduction by an incremental flow that is less than the value of $LPM_{ObsDiag}$. In a preferred embodiment, the present invention does not detect an inflow obstruction based on only the smaller increase in pump flow, but may require simultaneous change in pulsatility index in order to decide on the presence or absence of an inflow obstruction.

More specifically, an inflow or outflow obstruction may be determined as shown in FIG. 7. When pump speed is reduced and the resultant pump flow increases while pulsatility index decreases, then an inflow obstruction is detected. On the other hand, when the speed reduction creates a decreased resultant flow together with an increased pulsatility index, then an outflow obstruction is detected.

The present invention may also distinguish between different levels of confidence in judging the presence of inflow and outflow obstructions for a saturated flow condition. For example, a large jump in flow being produced by a reduction in pump speed may always generate an indication of an inflow obstruction. Depending on whether pulsatility experiences a large drop or a small drop, the confidence of the inflow obstruction may be characterized as either probable or possible, respectively. As further shown in FIG. 8, a small jump in flow may correlate with a likely inflow obstruction if the pulsatility also experienced a large drop. If both the jump in pump flow and the drop in pulsatility are small (i.e., less than respective thresholds), then the diagnostic decision may correspond to a "no call" with respect to whether there is any obstruction or a saturated flow.

When a reduced speed generates neither a large change in flow nor a large change in pulsatility, then a saturated flow may be detected. In the presence of a saturated flow, it may be desirable to reduce pump speed to the lowest value that maintains the current flow value.

An outflow obstruction may be detected according to FIG. 8 when a large drop in the flow is correlated with the reduction in pump speed. If the large drop in flow occurs with a large jump in pulsatility, then an outflow obstruction is probable. If associated with a small jump in pulsatility, then an outflow obstruction is classified as possible. When a small drop in pump flow occurs with a large jump in pulsatility, then an outflow obstruction is classified as likely, but if coupled with a small jump in pulsatility then no call is made.

Figure 9:
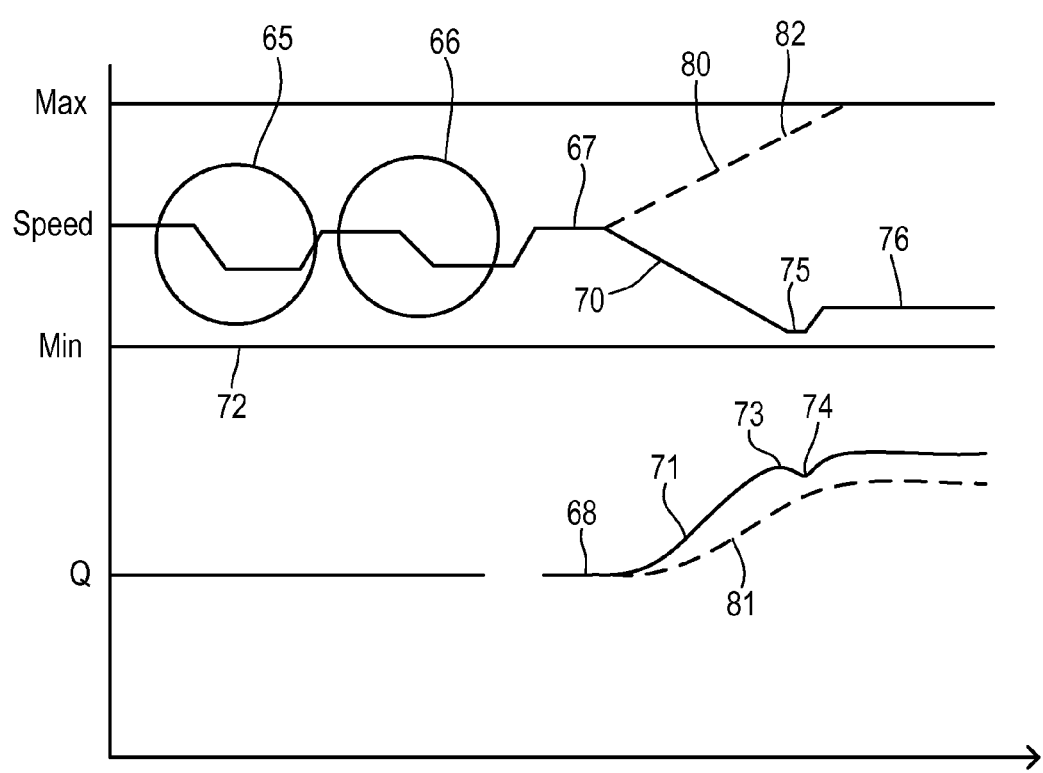
FIG. 9 is a graph showing pump speed adjustments and resultant changes in flow when correcting for a detected obstruction.

Based on the confidence with which either an inflow or an outflow obstruction is detected, corresponding measures can be taken to attempt to provide a greater flow or even restore the flow at least the expected minimum flow. As shown in FIG. 9, a plurality of speed modification trials including trials 65 and 66 are performed in order to assess the most likely obstruction. Prior to the corrective action, the pump speed has a setpoint 67 and a corresponding flow value 68. When an inflow obstruction is present, corrective action comprises gradually decreasing the pump speed at 70 to produce a gradual increase in flow at 71. A predetermined minimum speed 72 may preferably have been established by the physician based on the physiology of the patient, and if the speed reaches that minimum then no further changes would be made. As long as further decreases in speed along line 70 generate a corresponding increase in pump flow along 71, then the speed continues to decrease. When the resultant flow reaches a peak at 73 and then decreases at 74, the reduction in pump speed ceases at 75. Then the speed achieving the highest flow is adopted at 76.

In the case of a detected outflow obstruction, corrective action comprises increasing the pump speed at 80 which results in an increased pump flow at 81. The increase may continue until either reaching a maximum pump speed 82 as previously determined by a physician or until pump flow reaches the expected minimum flow.

Figure 10:
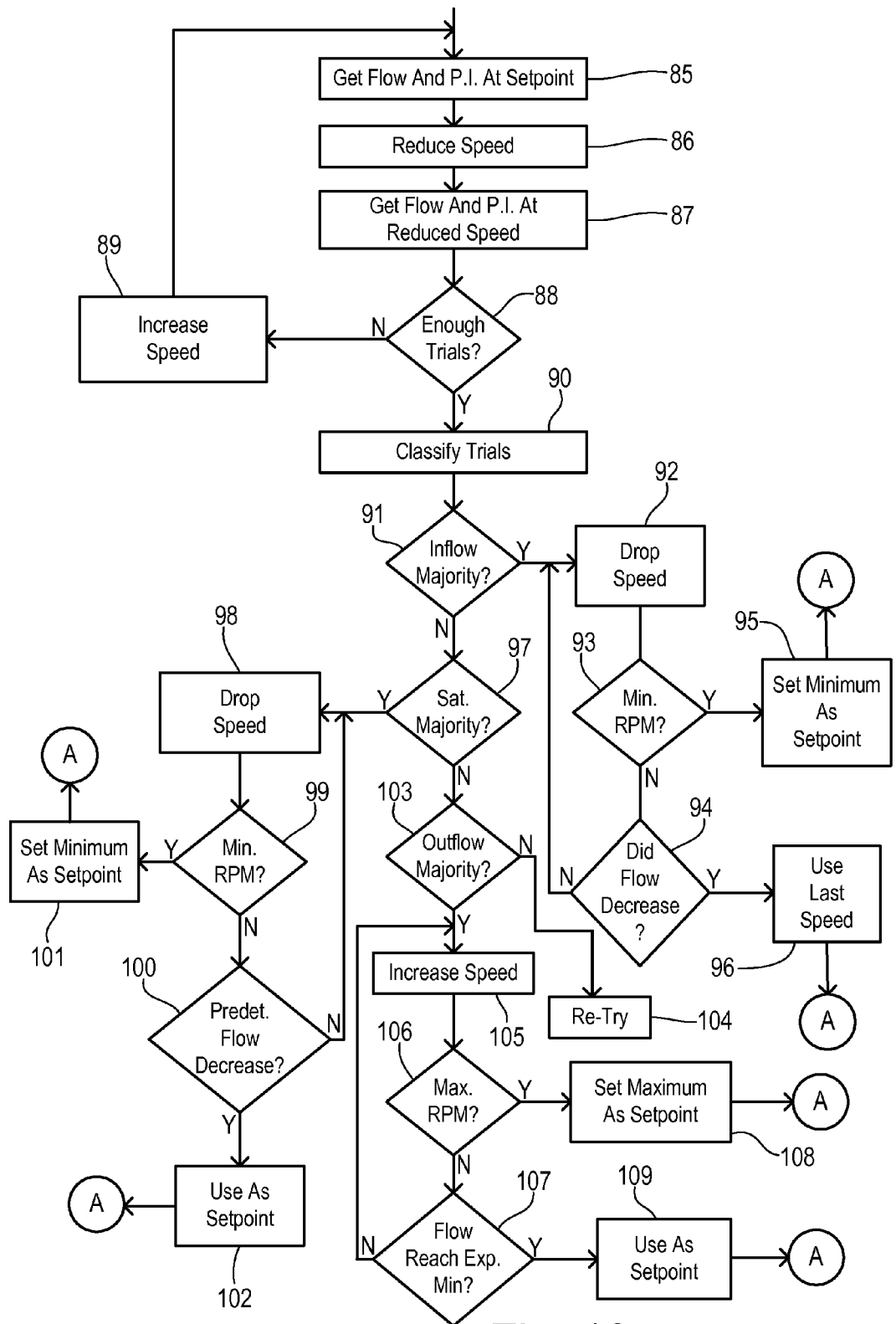
FIG. 10 is a flowchart showing a further method of the invention.

The plurality of trials and the corrective actions are further described in the method of FIG. 10. In step 85, an actual flow value and a pulsatility index are measured at the current speed setpoint. In step 86, the pump speed is reduced by a preset amount. In step 87, a new flow value and pulsatility index are measured at the reduced speed. A check is made in step 88 to determine whether a predetermined number of trials have been obtained. If not, speed is increased back to the original setpoint in step 89 and a return is made to step 85.

Once sufficient trials have been conducted, the trials are classified in step 90. Classification of each trial is performed in accordance with FIG. 8, for example. The classified trials are then examined statistically in order to ensure that sufficient data is present to indicate either an inflow obstruction, outflow obstruction, or saturated flow. In a preferred embodiment, a majority of trials must indicate a respective condition. In step 91, a check is made to determine whether a majority of trials indicate that an inflow obstruction is either likely, possible, or probable. If so, then corrective action to increase pump flow begins at step 92 by dropping the pump speed by a predetermined amount. A check is performed in step 93 to determine whether the speed has been reduced to a predetermined minimum speed. If not, then a check is performed in step 94 to determine whether the latest drop in speed has instead caused a flow decrease. If not, then a return is made to step 92 to drop the speed once again. If a minimum speed is reached in step 93, then the minimum speed is set as a new speed setpoint and the method returns to point A in FIG. 3. In FIG. 3, the method waits during a predetermined wait time ($T_{EndDiagWait}$) in step 110 before returning to normal operation. This periodic return to normal operation ensures that nominal operation is utilized whenever possible.

Returning to FIG. 10, in the event that a flow decrease is detected in step 94 then the speed setpoint is set to the last speed that obtained a flow increase in step 96 and a return is made to point A.

If there are not a majority of trials detecting an inflow obstruction in step 91, then a check is made in step 97 to determine whether a majority of trials indicate a saturated flow. If they do, then pump speed is dropped by a predetermined amount in step 98. A check is performed in step 99 to determine whether a minimum speed has been reached. If not, then a check is made in step 100 to determine whether a predetermined flow decrease has occurred (i.e., whether the flow has become unsaturated). If not, then a return is made to step 98 to drop speed once again. If a minimum speed is reached in step 99, then the minimum speed is adopted as a new speed setpoint and the method returns to point A. If a flow decrease is detected in step 100, then the current speed is used as a new speed setpoint and a return is made to point A.

If a majority of trials do not indicate a saturated flow condition in step 97, then a check is made in step 103 to determine whether a majority of trials indicated that an outflow obstruction is likely, possible, or probable. If not, then the flow problem has not been properly diagnosed and the method may retry to diagnose the obstruction in step 104 (e.g., by repeating a new plurality of trials at step 85). If a majority of trials indicate an outflow obstruction, then pump speed is increased by a set amount in step 105. A check is made in step 106 to determine whether a maximum speed has been reached. If not, then a check is made in step 107 to determine whether the result flow has reached the expected minimum flow value. If not, then a return is made to step 105 to further increase the speed. If a maximum speed is detected in step 106, then the maximum speed is adopted as a new speed setpoint in step 108 and a return is made to point A. If the flow reaches the expected minimum flow value in step 107, then the current speed is used as a new speed setpoint in step 109 and a return is made to point A.

Figure 11:
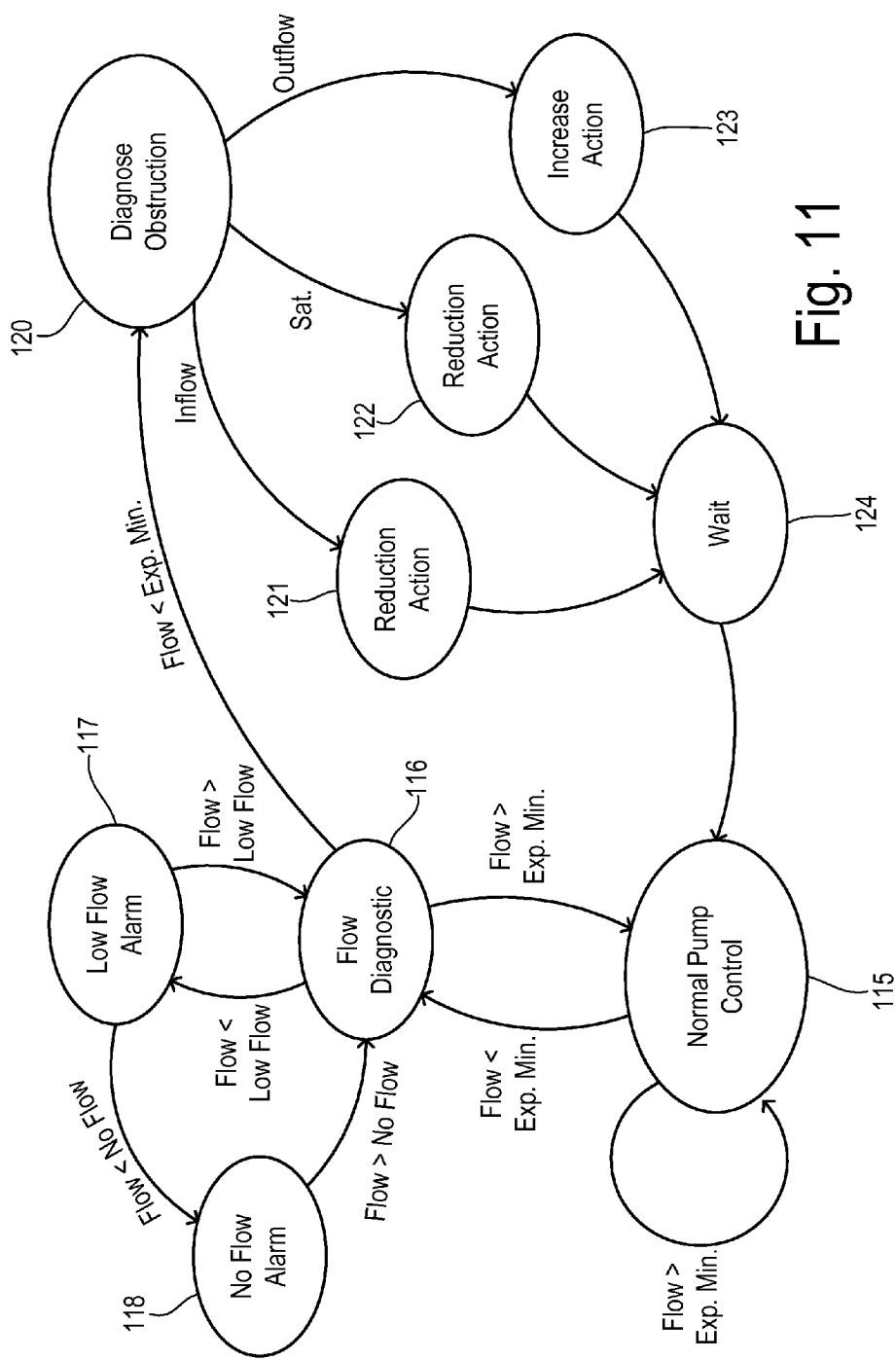
FIG. 11 is a state diagram corresponding to another preferred embodiment.

The present invention can also be understood using a state diagram as shown in FIG. 11. State 115 is a normal pump control state wherein pump control may be implemented as according to U.S. Pat. No. 7,160,243, for example. As long as an actual flow remains greater than the expected minimum flow, operation continues to remain in state 115. When pump flow falls below the expected minimum flow for greater than time $T_{FlowDiagWait}$, then a transition is made from state 115 to a flow diagnostic state 116. A transition is made back from state 116 to state 115 when the flow value remains above the expected minimum flow for greater than $T_{FlowDiagWait}$. State 116 also checks for low flow. Thus, if actual flow falls below the low flow threshold for greater than a time $T_{LowFlow}$ then a transition is made to a low flow alarm state 117. A transition would be made back from state 117 to 116 whenever the actual flow remains greater than the low flow threshold for greater than $T_{LowFlow}$. State 117 monitors for a no flow condition by comparing actual flow with a no flow threshold. If actual flow is less than the no flow threshold for at least time $T_{NoFlow}$ then a transition is made to a no flow alarm state 118. Flow continues to be compared with the no flow threshold and if it remains above the no flow threshold for at least $T_{NoFlow}$ then a transition is made back to flow diagnostic state 116.

While in state 116, actual flow continues to be compared to the expected minimum flow value and if it remains below it for greater than a time $T_{ObsDiagWait}$, then a transition is made to diagnose obstruction state 120. While in state 120, a plurality of trials are conducted by modifying the pump speed in order to attempt to classify either an inflow obstruction, outflow obstruction, or saturated flow condition. When an inflow obstruction is detected, a transition is made to state 121 for executing a speed reduction action. When an outflow obstruction is detected, then a transition is made to state 123 for executing a speed increase action. When a saturated flow condition is detected, a transition is made to state 122 for executing a speed reduction action. After the actions in states 121-123, transitions are made to wait state 124 wherein the pump continues to operate at a new speed setpoint, thus achieving the best flow results obtainable under current conditions. After a wait time ($T_{EndDiagWait}$) corresponding to an expected time in which conditions may eventually change, a transition is made back to normal pump control state 115 with a possible reintroduction of corrective speed changes if flow again does not exceed the expected minimum flow.

What is claimed is:

1. A method of controlling blood flow delivered to a patient by a left ventricle assist device including a pump, comprising the steps of:
   collecting blood flow measurements during operation of the pump;
   identifying an impaired flow condition when a plurality of successive blood flow measurements are between an expected flow and a low flow, wherein the low flow would necessitate issuing an alert;
   during the impaired flow condition, detecting whether an inflow obstruction exists by determining whether a reduction in speed of the pump is correlated with a predetermined increase in the blood flow measurements; and
   if the inflow obstruction is detected, then further reducing the speed of the pump to further increase the blood flow measurements.

2. A method of controlling blood flow delivered to a patient by a left ventricle assist device including a pump, comprising the steps of:
   collecting blood flow measurements during operation of the pump;
   identifying an impaired flow condition when a plurality of successive blood flow measurements are between an expected flow and a low flow, wherein the low flow would necessitate issuing an alert;
   during the impaired flow condition, detecting whether an inflow obstruction exists by determining whether a reduction in speed of the pump is correlated with a predetermined increase in the blood flow measurements;
   if the inflow obstruction is detected, then further reducing the speed of the pump to further increase the blood flow measurements;
   during the impaired flow condition and if the inflow obstruction is not detected, then detecting whether an outflow obstruction exists by determining whether a reduction in speed of the pump is correlated with a predetermined decrease in the blood flow measurements; and
   if the outflow obstruction is detected, then increasing the speed of the pump to increase the blood flow measurements.

3. A system for coupling to a patient to assist blood flow in the patient, comprising:

a pump adapted to receive an inflow of blood from the patient and to provide an outflow of blood back to the patient;

a motor coupled to rotate the pump at a selectable speed;

a controller coupled to the motor and adapted to drive the motor at a target speed via a driver signal generated by the controller, wherein the controller is configured for:

collecting blood flow measurements during operation of the pump;

identifying an impaired flow condition when a plurality of successive blood flow measurements are between an expected flow and a low flow, wherein the low flow would necessitate issuing an alert;

during the impaired flow condition, detecting whether an inflow obstruction exists by determining whether a reduction in speed of the pump is correlated with a predetermined increase in the blood flow measurements; and if the inflow obstruction is detected, then further reducing the speed of the pump to further increase the blood flow measurements.

4. A system for coupling to a patient to assist blood flow in the patient, comprising:

a pump adapted to receive an inflow of blood from the patient and to provide an outflow of blood back to the patient;

a motor coupled to rotate the pump at a selectable speed;

a controller coupled to the motor and adapted to drive the motor at a target speed via a driver signal generated by the controller, wherein the controller is configured for:

collecting blood flow measurements during operation of the pump;

identifying an impaired flow condition when a plurality of successive blood flow measurements are between an expected flow and a low flow, wherein the low flow would necessitate issuing an alert;

during the impaired flow condition, detecting whether an inflow obstruction exists by determining whether a reduction in speed of the pump is correlated with a predetermined increase in the blood flow measurements;

if the inflow obstruction is detected, then further reducing the speed of the pump to further increase the blood flow measurements;

during the impaired flow condition and if the inflow obstruction is not detected, then detecting whether an outflow obstruction exists by determining whether a reduction in speed of the pump is correlated with a predetermined decrease in the blood flow measurements; and if the outflow obstruction is detected, then increasing the speed of the pump to increase the blood flow measurements.

* * * * *